US011574734B1

(12) United States Patent
Gill et al.

(10) Patent No.: US 11,574,734 B1
(45) Date of Patent: *Feb. 7, 2023

(54) METHODS AND SYSTEMS FOR EXCHANGE OF EQUIPMENT PERFORMANCE DATA

(71) Applicant: ENDRA Life Sciences Inc., Ann Arbor, MI (US)

(72) Inventors: Jeremy Gill, London (CA); Michael M. Thornton, London (CA)

(73) Assignee: ENDRA Life Sciences Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/861,927

(22) Filed: Jul. 11, 2022

Related U.S. Application Data

(63) Continuation of application No. 17/680,094, filed on Feb. 24, 2022, now Pat. No. 11,405,470, which is a (Continued)

(51) Int. Cl.
   *G06F 11/00* (2006.01)
   *G16H 40/40* (2018.01)
   (Continued)

(52) U.S. Cl.
   CPC ......... *G16H 40/40* (2018.01); *G06F 11/3006* (2013.01); *G06F 11/3075* (2013.01);
   (Continued)

(58) Field of Classification Search
   CPC ............... G06F 11/079; G06F 11/3058; G06F 11/3409; G06F 11/3466; G06F 11/0742;
   (Continued)

(56) References Cited

U.S. PATENT DOCUMENTS

| 10,585,788 B2* | 3/2020 | Nallabothula ...... G06F 11/3688 |
| 2013/0032634 A1* | 2/2013 | McKirdy ............. A61B 5/0205 |
| | | 235/375 |
| 2020/0133698 A1* | 4/2020 | Permenter ........... G06F 11/0709 |

* cited by examiner

*Primary Examiner* — Charles Ehne
(74) *Attorney, Agent, or Firm* — Stanley E. Jelic

(57) ABSTRACT

A method for exchange of equipment performance data includes the steps of: obtaining performance data of a communicatively-insulated device; converting the performance data into a scannable code; capturing an image of the scannable code; decoding the scannable code using a communicatively-enabled device to extract an address string encoded in the scannable code, the address string comprising an address of a remote server and the performance data; initiating, by the communicatively-enabled device, a communications link with the remote server using the address string thereby to provide the performance data to the remote server; performing, by the remote server, analytics on the performance data; and sending historic device performance data and/or analytical results to a remote computing device and/or sending a link to the historic device performance data and/or analytical results to the remote computing device; wherein the communicatively-insulated device is medical imaging equipment and wherein obtaining the performance data comprises scanning a phantom using the medical imaging equipment and/or acquiring medical imaging equipment sensor data and generating a system status report identifying one or more operational parameters of the medical imaging equipment.

10 Claims, 7 Drawing Sheets

Related U.S. Application Data continuation-in-part of application No. 17/504,331, filed on Oct. 18, 2021, now Pat. No. 11,314,617.

(51) Int. Cl.
*G06F 11/30* (2006.01)
*G06F 11/34* (2006.01)
*G06K 1/12* (2006.01)
*G06K 7/14* (2006.01)
*H04L 67/12* (2022.01)

(52) U.S. Cl.
CPC ...... *G06F 11/3409* (2013.01); *G06F 11/3466* (2013.01); *G06K 1/121* (2013.01); *G06K 7/1417* (2013.01); *H04L 67/12* (2013.01)

(58) Field of Classification Search
CPC ............. G06F 11/0748; G06F 11/0778; G06F 11/0793
See application file for complete search history.

METHODS AND SYSTEMS FOR EXCHANGE OF EQUIPMENT PERFORMANCE DATA

CROSS-REFERENCE TO RELATED APPLICATIONS

This application is a continuation of pending U.S. non-provisional application Ser. No. 17/680,094, filed Feb. 24, 2022, which is a continuation-in-part of patented U.S. non-provisional application Ser. No. 17/504,331, filed Oct. 18, 2021, both of which are herein incorporated by reference in their entirety.

FIELD

The subject disclosure relates generally to methods and systems for exchange of equipment performance data.

BACKGROUND

In today's world, it is common place to provide devices with the ability to communicate freely over wireless and/or wired networks with other devices. That said, there are many instances where it is not possible or undesired for devices to communicate freely in this manner. These devices can be communicatively-insulated for a variety of reasons. For example, many legacy devices, which were manufactured without such communications capabilities, are still in existence and remain in use. In some environments, connectivity of devices is limited to reduce the risk of third-party hacking attempts, unwanted access to sensitive information, or other reasons. This may be the result of firewalls and/or other security measures or may simply be the choices of device owners. In some environments, connectivity of devices is limited as a result of geographical location.

As will be appreciated, when devices are communicatively-insulated, monitoring performance and running analytics remotely may present challenges. Not surprisingly, improvements in the monitoring and assessment of communicatively-insulated devices are desired.

It is therefore an object to provide novel methods and systems for exchange of equipment performance data.

This background serves only to set a scene to allow a person skilled in the art to better appreciate the following brief and detailed descriptions. None of the above discussion should necessarily be taken as an acknowledgment that this discussion is part of the state of the art or is common general knowledge.

BRIEF DESCRIPTION

It should be appreciated that this brief description is provided to introduce a selection of concepts in a simplified form that are further described below in the detailed description. This brief description is not intended to be used to limit the scope of claimed subject matter.

Accordingly, in one aspect there is provided a method comprising: obtaining performance data of a communicatively-insulated device; converting the performance data into a scannable code; capturing an image of the scannable code; decoding the scannable code using a communicatively-enabled device to extract an address string encoded in the scannable code, the address string comprising an address of a remote server and the performance data; initiating, by the communicatively-enabled device, a communication link with the remote server using the address string thereby to provide the performance data to the remote server; performing, by the remote server, analytics on the performance data; and sending historic device performance data and/or analytical results to a remote computing device and/or sending a link to the historic device performance data and/or analytical results to the remote computing device; wherein the communicatively-insulated device is medical imaging equipment and wherein obtaining the performance data comprises scanning a phantom using the medical imaging equipment and/or acquiring medical imaging equipment sensor data and generating a system status report identifying one or more operational parameters of the medical imaging equipment.

In one or more embodiments, the method further comprises performing, by the remote server, analytics on the performance data.

In one or more embodiments, the method further comprises at least one of: sending historic device performance data and/or analytical results to a remote computing device; and sending a link to the historic device performance data and/or analytical results to the remote computing device. In one form, the communicatively-enabled device and the remote device may be the same device or may be different devices.

In one or more embodiments, the method comprises, prior to the converting, encoding the performance data. In one form, the encoding comprises serializing the performance data and transforming the serialized performance data to tamper-proof the performance data. In one form, transforming the serialized performance data comprises subjecting the serialized performance data to one of a check sum function or encryption program. In one form, the subjecting comprises subjecting the serialized performance data to the check sum function to generate a digital signature that is appended to the serialized performance data. In one form, the encoding further comprises sanitizing the transformed serialized performance data into an address string format and prepending the address of the remote server to the sanitized performance data thereby to form the address string.

In one or more embodiments, the scannable code is a matrix code. In one form, the matrix code is a quick response (QR) code.

In one or more embodiments, the method further comprises, after the converting, presenting the scannable code on a display console of the communicatively-insulated device and/or printing the scannable code on a physical medium.

In one or more embodiments, the method comprises capturing the image of the scannable code with the communicatively-enabled device.

According to another aspect there is provided a method comprising: receiving, by a server, a network connection request from a communicatively-enabled device, the network connection request comprising an address string extracted from an image of a scannable code, the address string comprising an address of the server and performance data of a communicatively-insulated device; extracting, by the server, from network connection request the performance data; and verifying, by the server, the performance data.

In one or more embodiments, the verifying comprises: subjecting the extracted performance data to a check sum function to generate a signature; and comparing the generated signature to a signature within the address string to determine whether the signature and generated signature match.

In one or more embodiments, the method further comprises compiling, by the server, the performance data with prior performance data in a database to create historic performance data.

In one of more embodiments, the method further comprises running analytics on the performance data.

In one or more embodiments, the method further comprises at least one of: transmitting the historic performance data and/or results of the analytics to a remote computing device; and transmitting a link to the historic performance data and/or results of the analytics to the remote computing device.

BRIEF DESCRIPTION OF THE DRAWINGS

Embodiments will now be described more fully with reference to the accompany drawings in which.

DETAILED DESCRIPTION

Figure 1:
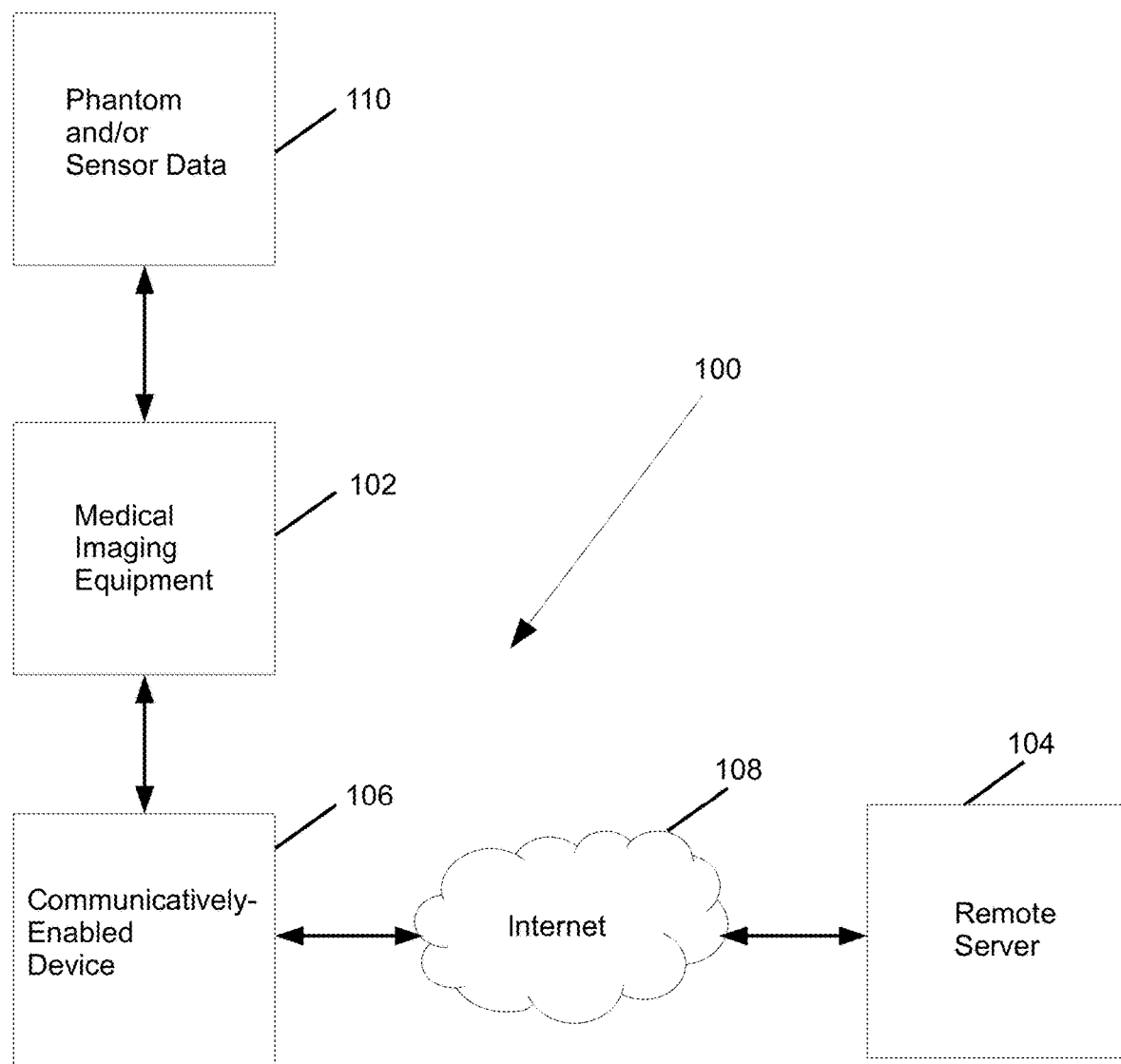
FIG. 1 is a schematic diagram of a system for exchange of medical imaging equipment performance data.

The foregoing brief description, as well as the following detailed description of certain examples will be better understood when read in conjunction with the accompanying drawings. As used herein, a feature, structure, element, component etc. introduced in the singular and preceded by the word "a" or "an" should be understood as not necessarily excluding the plural of the features, structures, elements, components etc. Further, references to "one example" or "one embodiment" are not intended to be interpreted as excluding the existence of additional examples or embodiments that also incorporate the described features, structures, elements, components etc.

Unless explicitly stated to the contrary, examples or embodiments "comprising" or "having" or "including" a feature, structure, element, component etc. or a plurality of features, structures, elements, components etc. having a particular property may include additional features, structures, elements, components etc. not having that property. Also, it will be appreciated that the terms "comprises", "has", "includes" means "including but not limited to" and the terms "comprising", "having" and "including" have equivalent meanings.

As used herein, the term "and/or" can include any and all combinations of one or more of the associated listed features, structures, elements, components or other subject matter.

Reference herein to "example" means that one or more feature, structure, element, component, characteristic and/or operational step described in connection with the example is included in at least one embodiment and/or implementation of the subject matter according to the subject disclosure. Thus, the phrases "an example," "another example," and similar language throughout the subject disclosure may, but do not necessarily, refer to the same example. Further, the subject matter characterizing any one example may, but does not necessarily, include the subject matter characterizing any other example.

Reference herein to "configured", "operative", and "adapted" denote actual states that fundamentally tie the feature, structure, element, component, or other subject matter to the physical characteristics of the feature, structure, element, component or other subject matter preceding the phrase "configured to", "operative to", and "adapted to". Thus, "configured", "operative", and "adapted" means that the feature, structure, element, component or other subject matter is designed and/or intended to perform a given function. As a result, the use of the term "configured", "operative", and "adapted" should not be construed to mean that a given feature, structure, element, component, or other subject matter is simply "capable of" performing a given function but that the feature, structure, element, component, and/or other subject matter is specifically selected, created, implemented, utilized, and/or designed for the purpose of performing the function.

Unless otherwise indicated, the terms "first," "second," etc. are used herein merely as labels, and are not intended to impose ordinal, positional, or hierarchical requirements on the items to which these terms refer. Moreover, reference to a "second" item does not require or preclude the existence of a lower-numbered item (e.g., a "first" item) and/or a higher-numbered item (e.g., a "third" item).

As used herein, the terms "approximately", "about", "substantially", "generally" etc. represent an amount or condition close to the stated amount or condition that results in the desired function being performed or the desired result being achieved. For example, the terms "approximately", "about", "substantially", "generally" etc. may refer to an amount or condition that is within engineering tolerances to the precise value or condition specified that would be readily appreciated by a person skilled in the art.

In general, methods and systems for exchange of equipment performance data are described herein. The methods and systems are particularly suited to allow operation of communicatively-insulated equipment to be monitored and assessed. In this manner, the communicatively-insulated equipment may be serviced, if required, and its operation calibrated despite a lack of direct or unimpeded connectivity with the equipment manufacturer/supplier or maintenance/service provider.

Communicatively-insulated within the context of the subject application refers to equipment whose communication capabilities involving performance or other selected data is inhibited or limited or constrained intentionally or otherwise. For example, the communicatively-insulated equipment may be legacy equipment devoid of communication capabilities. The communicatively-insulated equipment may be located in a remote geographical location where establishing communications links is difficult or impossible. The communicatively-insulated equipment may be located in an environment where firewalls and/or other security measures inhibits or limits the ability of the communicatively-insulated equipment to establish communication links with external devices. The communication capabilities of the communicatively-insulated equipment may be constrained to inhibit certain data from being displayed or presented or to avoid certain data from having to be downloaded directly from the communicatively-insulated equipment by on-site personnel.

In one form, the method comprises obtaining performance data of a communicatively-insulated device and converting the performance data into a scannable code. An image of the scannable code is captured and the scannable code is decoded using a communicatively-enabled device to extract an address string encoded in the scannable code. The address string comprises an address of a remote server and the performance data. A communications link with the remote server is initiated by the communicatively-enabled device using the address string thereby to provide the performance data to the remote server. The remote server extracts the performance data from the address string and verifies the performance data. Once verified, the performance data is compiled with historic performance data and/or analytics are run on the performance data to assess the operation of the communicatively-insulated device. Feedback can then be provided to the owner/operator of the communicatively-insulated device either by transmitting the historic performance data and/or results of the analytics to the owner/operator of the device or by transmitting a link to the historic performance data and/or results of the analytics to the owner/operator of the communicatively-insulated device. Further specifics concerning the methods and systems will now be described.

Turning now to FIG. 1, a system for exchange of equipment performance data is shown and is generally identified by reference character 100. In this embodiment, the equipment is medical imaging equipment 102 that is communicatively-insulated. The medical imaging equipment 102 may be a standalone device with its own display and processing capabilities. Alternatively, the medical imaging equipment 102 may comprise an imaging unit that communicates via a local or wide area network with one or more computing devices that provide display and processing capabilities over wired and/or wireless communication links. For example, the medical imaging equipment 102 may be a thermoacoustic (TA) imaging system, an ultrasound (US) imaging system, a magnetic resonance (MR) imaging system, or a computed tomography (CT) imaging system. Of course, the medical imaging equipment 102 may take other forms such as therapy equipment.

As will be appreciated by those of skill in the art, the medical imaging equipment 102 acquires sensitive patient data and therefore is typically located in an environment where connectivity of the medical imaging equipment to external computing devices (e.g. computing devices outside of its network) is inhibited or limited.

A remote server 104 such as a web server associated with the manufacturer of the medical imaging equipment 102 or an associate or affiliate of the medical imaging equipment manufacturer is configured to receive performance data of the medical imaging equipment 102 from a communicatively-enabled device 106 and process the received performance data to allow the performance of the medical imaging equipment 102 to be monitored and assessed. The remote server 104, as is well known to those of skill in the art, comprises, for example, one or more processors, system memory (volatile and/or non-volatile memory), other non-removable or removable memory (e.g., a hard disk drive, RAM, ROM, EEPROM, CD-ROM, DVD, flash memory, etc.) and a system bus coupling the various computer components to the one or more processors.

In this embodiment, the communicatively-enabled device 106 is a smart mobile or cellular phone, tablet or pad computing device or other portable computing device that has image capture and Internet communication capabilities. Devices of this nature are well known to those of skill in the art and as such, details of the communicatively-enabled device 106 will not be described herein. The communicatively-enabled device 106 is operable to capture an image of encoded performance data generated by the medical imaging equipment 102 and transmit the encoded performance data to the remote server 104 over a communications link such as an Internet connection 108 as will be described.

Figure 2:
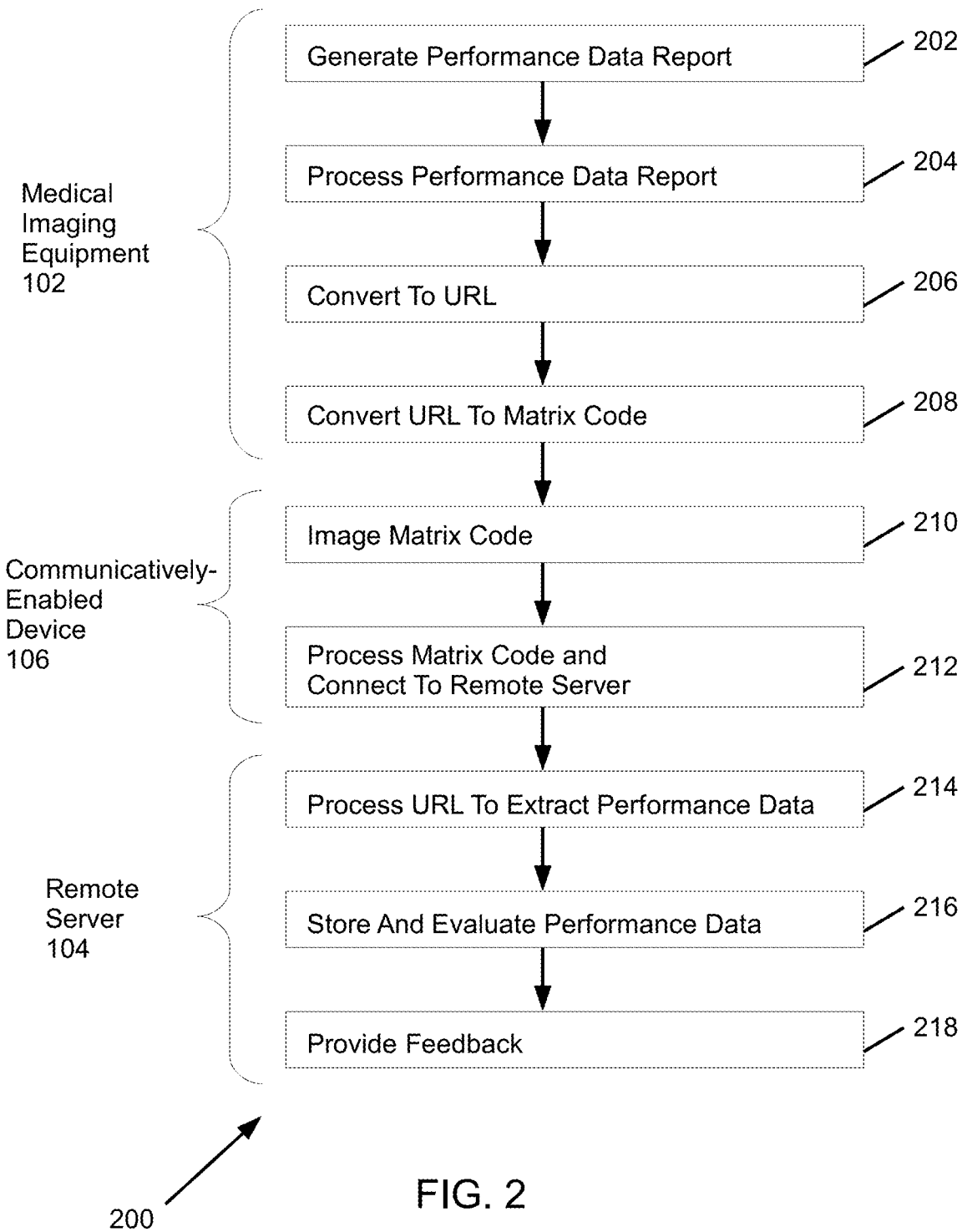
FIG. 2 is a flowchart of a method for exchange of medical imaging equipment performance data carried out by the system of FIG. 1.

In the subject embodiment, in order to allow the operation of the medical imaging equipment 102 to be monitored and assessed, the medical imaging equipment 102 has a diagnostic application installed therein. The diagnostic application can be run in response to operator input or can be run automatically at programmed intervals. In general, when the diagnostic application is initiated, a performance data exchange method generally identified by reference numeral 200 as shown in FIG. 2 is carried out. In particular, when the diagnostic application is initiated, a report comprising performance data of the medical imaging equipment 102 is generated (step 202). The performance data of the report is then processed to encode and secure the performance data (step 204) and the processed performance data is appended to a uniform resource locator (URL) (i.e., web address) of the remote server 104 (step 206). The URL that includes the performance data is then converted into a scannable matrix code such as a quick response (QR) code and presented by displaying the URL on a display console, screen, monitor or the like of the medical imaging equipment 102 and/or by printing the URL on a physical medium (step 208). The presented matrix code can then be imaged by the communicatively-enabled device 106 (step 210).

Once imaged, the communicatively-enabled device 106 can be conditioned to process and decode the matrix code to extract the URL and then use the URL to establish an Internet connection with the remote server 104 (step 212). The remote server 104 in response to the established Internet connection processes the URL to extract the performance data of the medical imaging equipment 102 (step 214). The performance data is then stored by the remote server 104 in an internal database and evaluated thereby to allow the operation of the medical imaging equipment 102 to be monitored and assessed (step 216). Feedback concerning the operation of the medical imaging equipment 102 can then be provided to the owner/operator of the medical imaging equipment 102 allowing the medical imaging equipment to be re-calibrated if required (step 218).

Figure 3:
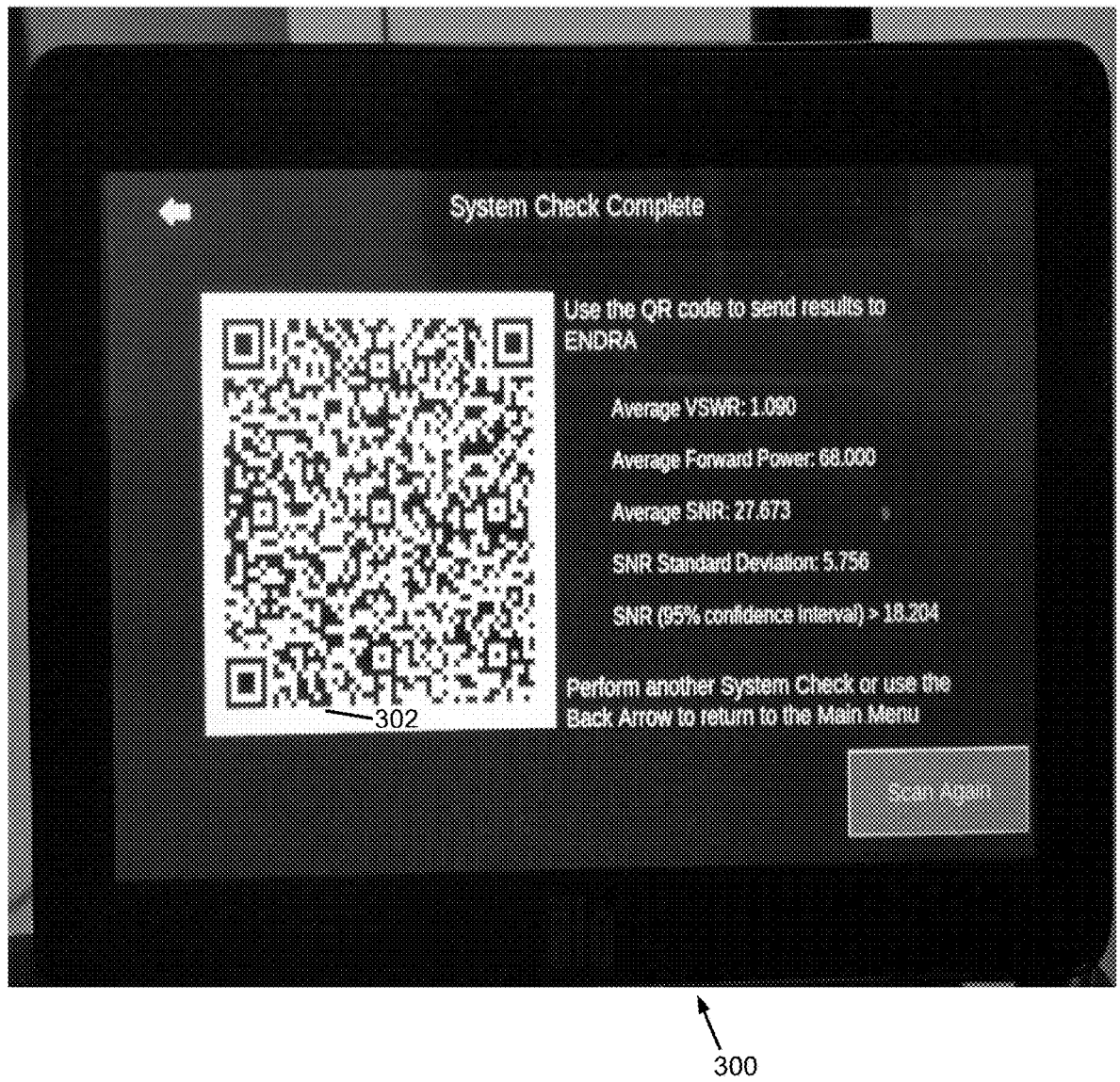
FIG. 3 is a system status report comprising performance parameters of the medical imaging equipment and a matrix code comprising the system status report presented on a display console of the medical imaging equipment.

In this embodiment, when the diagnostic application is initialized at step 202, the medical imaging equipment 102 is conditioned to scan or image a known performance target such as a phantom 110 and/or acquire data from on-board sensors of the medical imaging equipment 102. Once the known performance target has been scanned or imaged and/or on-board sensor data acquired, performance data in the form of a system status report is auto-generated by the medical imaging equipment 102 and presented on the display console of the medical imaging equipment 102 as shown in FIG. 3. In this example, the system status report identifies a plurality of performance parameters 300 of the medical imaging equipment 102 such as the average voltage standing wave ratio (VSWR), the average forward power, the average signal-to-noise ratio (SNR), the SNR standard deviation, and the SNR of the medical imaging equipment 102. Those of skill in the art will however appreciate that the system status report may identify fewer or more performance parameters of the medical imaging equipment 102.

Following generation of the system status report, as described above, the system status report is then processed at step 204 and converted to the URL at step 206. The URL is then converted to the matrix code 302 and presented on the display console of the medical imaging equipment 102 and/or printed on the physical medium. Those of skill in the art will also appreciate that the system status report need not be presented on the display console of the medical imaging equipment 102. Once generated, the system status report may be converted directly to the URL and then to the matrix code 302 so that only the matrix code is presented on the display console of the medical imaging equipment 102.

Figure 4:
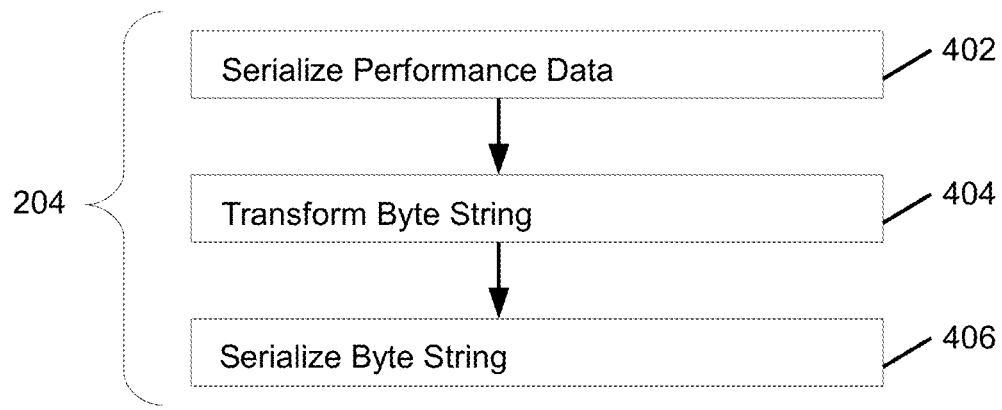
FIG. 4 is a flowchart of performance data processing performed during the method of FIG. 2.

Turning now to FIG. 4, the steps performed during processing of the performance data at step 204 of FIG. 2 are illustrated. As can be seen, the performance data is initially serialized to convert the performance data into a binary byte string (step 402). In this embodiment, Google protocol buffers are employed to convert the performance data into the binary byte string. Once serialized, the binary byte string of performance data is transformed to secure the binary byte string thereby to tamper-proof the performance data (step 404). This ensures the integrity of the performance data. In this embodiment, the serialized binary byte string of performance data is digitally signed by subjecting the binary byte string to a check sum function such as a SHA1 hash function to generate a symmetric hash-based authentication code (HMAC) typically 160 bits in length. The HMAC is then prepended as a header to the binary byte string. Those of skill in the art will however appreciate that alternative methods of transforming the serialized binary byte string of performance data may be employed. For example, the serialized binary byte string of performance data may be transformed using x509 public key encryption, pretty good privacy (PGP) encryption, saltpack, etc.

Following the digital signing of the serialized binary byte string of performance data, the digitally signed binary byte stream, which comprises the HMAC header and serialized binary byte string, is sanitized to facilitate transmission over the Internet connection 108 (step 406). In this embodiment during sanitization, the digitally signed binary byte stream is converted to a base64 representation, which is URL safe.

At step 206, an URL identifying the remote server 14 and one or more server route paths is then prepended to the base64 representation to yield an address string. In this embodiment, the resulting address string is a HTTP/1 GET-style URL of the form for example, https://webservername/webserverroutepath(s)/base64-encoded-byte-string. At step 208, the URL is then converted into the QR code 302 using a standard QR-code library and the QR code is presented on the display console of the medical imaging equipment 102 and/or printed on the physical medium.

Once presented on the display console of the medical imaging equipment 102 and/or printed on the physical medium, an image of the QR code 302 can be captured via the communicatively-enabled device 106. When an image of the QR code is captured by the communicatively-enabled device 106, the QR code is decoded the communicatively-enabled device 106 resulting in the HTTP/1 GET-style URL being displayed within a web browser on the display screen on the communicatively-enabled device 106. When the user of the communicatively-enabled device 106 selects the displayed HTTP/1 GET-style URL, the communicatively-enabled device 106 transmits a HTTP GET request that is delivered over the Internet connection 108 to the remote server 104 identified in the URL.

Figure 5:
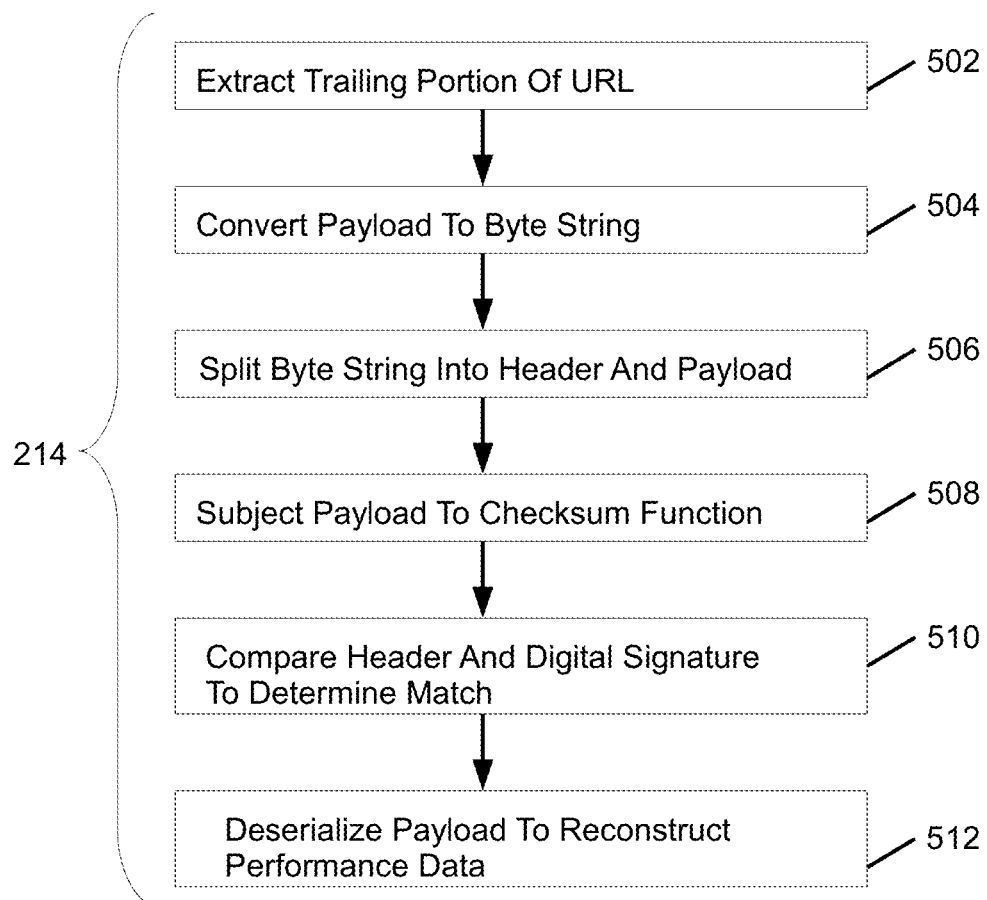
FIG. 5 is another flowchart of performance data processing performed during the method of FIG. 2.

Upon receipt of the HTTP GET request, the remote server 104 routes the HTTP GET request according to the server route path(s) identified in the URL and then processes the URL at step 214. FIG. 5 shows the steps performed during processing of the URL at step 214. In particular, during step 214 the remote server 104 extracts the trailing portion of the URL (i.e. the base64 representation of the digitally signed binary byte string) and interprets it as a base64-encoded payload (step 502). The remote server 104 then converts the base64-encoded payload back to a digitally signed binary byte string (step 504). The digitally signed binary byte string is then split by the remote server 104 into the HMAC header and the trailing payload (step 506). The remote server 104 then subjects the trailing payload to the same SHA1 hash function to generate another HMAC signature (step 508) and compares the HMAC signature of the trailing payload with the HMAC header (step 510). If the HMAC signature of the trailing payload matches the HMAC header, the remote server 104 determines that the trailing payload comprises valid performance data. If the HMAC signature of the trailing payload does not match the HMAC header, the remote server 104 ignores the trailing payload and generates an error message indicating that there is an error in the performance data.

If the trailing payload is determined to comprise valid performance data, the remote server 104 deserializes the trailing payload using Google protocol buffers for example to reconstruct the performance report (step 512). The remote server 104 then performs a check to determine if the performance report already exists in the internal database. If the performance report already exists in the internal database, the remote server 104 ignores the performance report and generates an error message indicating that the performance report is a duplicate.

Following the above at step 216, if the performance report does not exist in the internal database, the remote server 104 adds the performance report to the internal database and generates an accepted message. Once the performance report has been added to the internal database, analytics can be run on the performance data, for example to compare the performance report with past performance reports, operation standards/norms etc., to determine the operational health of the medical imaging equipment 102. The results of the analytics can then be used to update a dashboard. The dashboard or a link to the dashboard can then be transmitted to the owner/operator of the medical imaging equipment 102 over an Internet connection 108 (step 218) thereby to provide feedback to the owner/operator of the medical imaging equipment. During this step, the dashboard or link transmitted to the the owner/operator of the medical imaging equipment 102 may comprise calibration data to input into the medical imaging equipment 102 to re-calibrate the same. The calibration data may be provided in a form that facilitates input into the medical imaging input 102 and may take the form of a scannable code.

Figure 6:
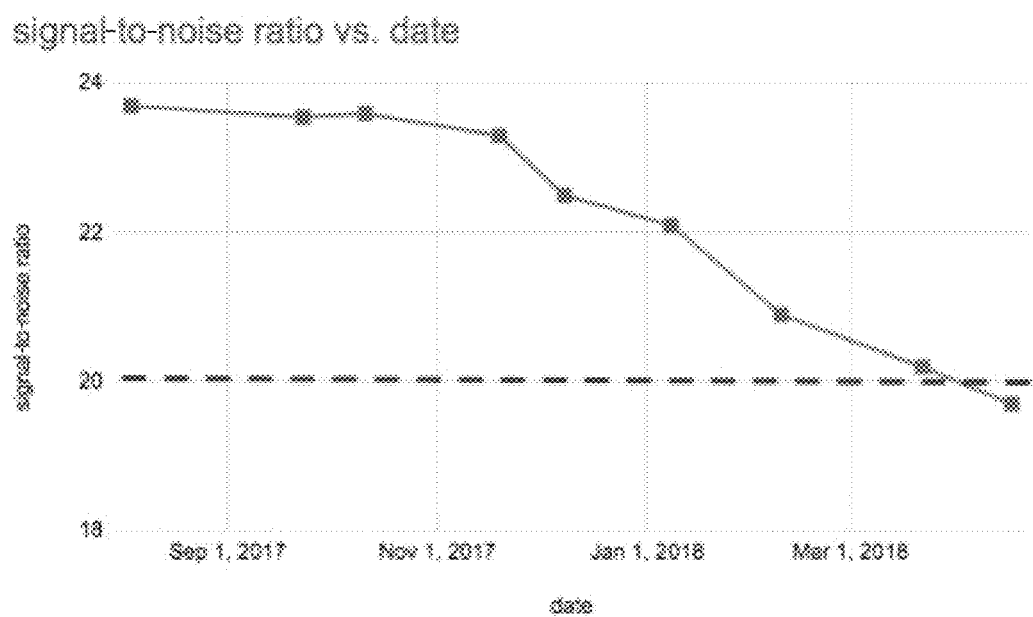
FIG. 6 is exemplary historical data generated by the system of FIG. 1.

For example, FIG. 6 shows exemplary historical data of the medical imaging equipment 102 that is accessible to the owner/operator of the medical imaging equipment. In particular, FIG. 6 shows system signal-to-noise (SNR) ratio results, derived from obtaining measurements for a quality assurance phantom, over a span of 9 months. For normal operation, the specified signal-to-noise for the medical imaging equipment is 20, or higher. The last measurement in April 2018 indicates that the medical imaging equipment is out of specification and should be serviced.

As will be appreciated by those of skill in the art, embodying the performance data of the medical imaging equipment 102 within a scannable code can be advantageous. For example, during servicing, presenting the performance data in this manner avoids sensitive performance data from being displayed thereby keeping diagnostic outputs of the medical imaging equipment 102 opaque to customers. Also, due to the sensitive nature of data acquired by the medical imaging equipment, service personnel may not be permitted to connect devices such as a laptop, jump drive etc. to the medical imaging equipment 102 to access the performance data. In such instances, embodying the performance data within the scannable code provides the service personnel access to the performance data and avoids service personnel from having to record displayed diagnostic outputs by hand, a series of images or video. Furthermore, embodying the performance data within the scannable code allows access to the performance data while avoiding the network and security policies of the environment within which the medical imaging equipment 102 is located. In addition, embodying the performance data within the scannable code allows the performance data to be readily transmitted for analysis reducing the need for on-site preventive maintenance visits.

In the systems and methods described above, the communicatively-enabled device 106 is described as capturing the image of the matrix code, decoding the matrix code to extract the URL of the remote server 104, and then establishing an Internet connection with the remote server. Those of skill in the art will appreciate that these steps may be performed in proximity to the medical imaging equipment 106 and in real-time after the image of the matrix code has been acquired. Alternatively, the communicatively-enabled device may be conditioned to establish the Internet connection with the remote server 104 well after the image of the matrix code has been captured, as may be required, if no Internet connection 108 is readily available at the time of image capture.

Those of skill in the art will appreciate that the image of the matrix code does not need to be acquired by the communicatively-enabled device 106. Instead, an imaging device 106 such as a conventional camera may be used to capture the image of the matrix code. The captured image can then be re-imaged or scanned off-site by the communicatively-enabled device 106 and processed as described above to allow the performance data to be uploaded to the remote server 104.

While specific reference is made to medical imaging equipment, those of skill in the art will appreciate that the equipment may take other forms. The subject methods are applicable to basically any communicatively-insulated equipment where it is desired to monitor and assess its performance.

Figure 7:
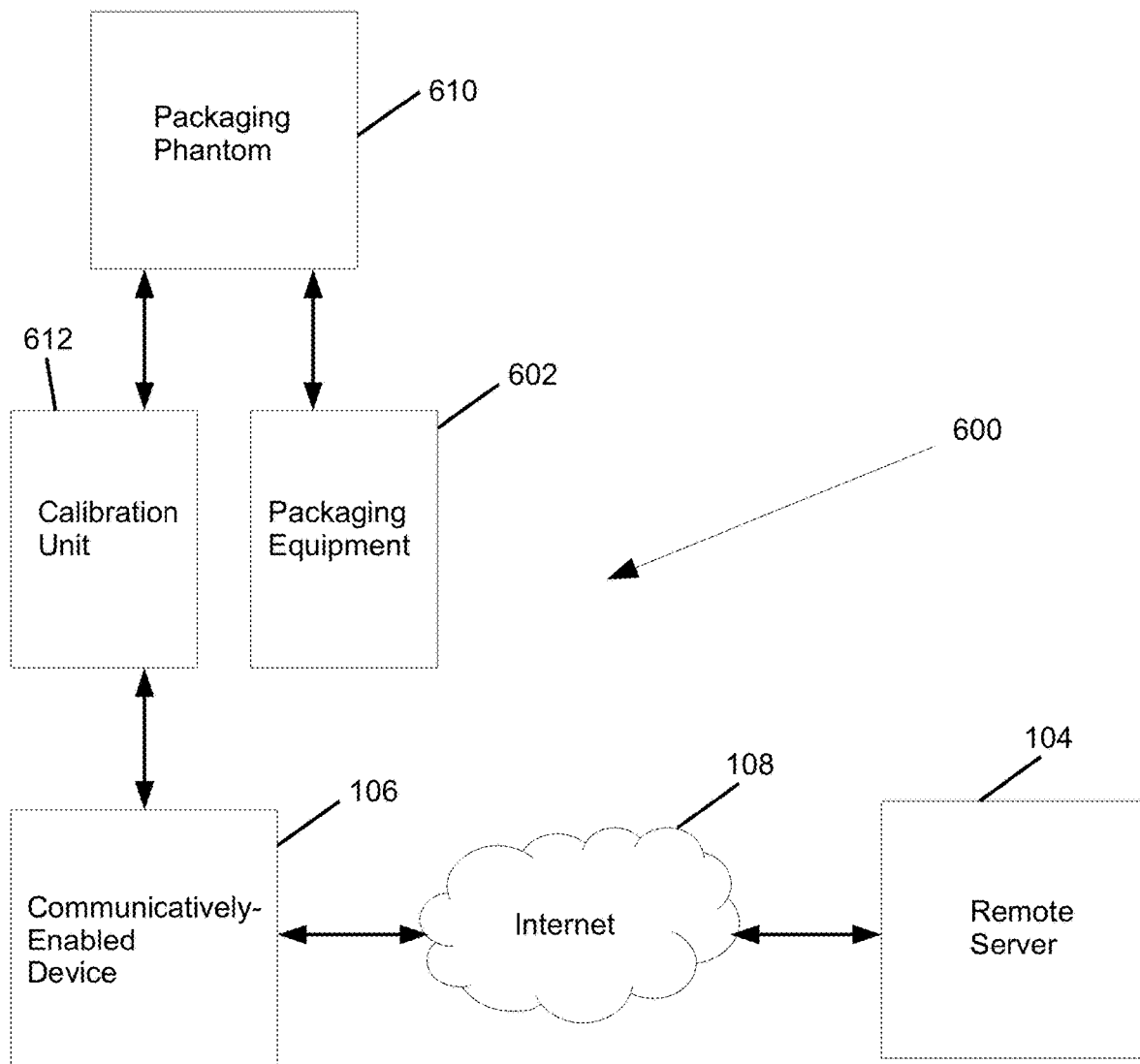
FIG. 7 is a schematic diagram of a system for exchange of packaging equipment performance data.

For example, turning now to FIG. 7, a system for exchange of packaging equipment performance data is shown and is generally identified by reference numeral 600. The system 600 is similar to system 100 illustrated in FIG. 1 and comprises communicatively-insulated packaging equipment 602 and a calibration unit 612. Similar to the previous embodiment, the system 600 also comprises a remote server 104 associated with the manufacturer of the packaging equipment 602 or an associate or affiliate of the packaging equipment manufacturer that is configured to receive performance data of the packaging equipment 602 from a communicatively-enabled device 606 and process the received performance data to allow the performance of the packaging equipment 602 to be monitored and assessed and calibration data returned to the owner/operator of the packaging equipment 602 thereby to allow the packaging equipment to be re-calibrated.

In this embodiment, when it is determined that the packaging equipment 602 has gone out of calibration or at any desired interval, a packaging phantom 610 is provided to the owner/operator of the packaging equipment 602 by the packaging equipment manufacturer. The packaging phantom 610 in this embodiment is a package to be run through the packaging equipment 602 to allow the packaging equipment 602 to perform its fill and seal operations. The packaging phantom 610 has markings printed or otherwise provided thereon that are scanned by the calibration unit 612 after the packaging operation has been performed on the packaging phantom 610. The calibration unit 612 in turn generates engineering codes representing the calibration state of the packaging equipment 602 and converts the engineering codes into a matrix code such as a QR code that can be scanned by the communicatively-enabled device 106 and processed in a manner similar to the previous embodiment thereby to allow the calibration state of the packaging equipment 602 to be assessed and re-calibration data provided back to the owner/operator of the packaging equipment 602, if required.

In one embodiment, calibration unit 612 and packaging equipment 602 are combined into the same sub-system, with or without the same housing.

As will be appreciated, the subject systems and methods allow performance data of communicatively-insulated equipment to be uploaded securely to a remote server without requiring user authentication through image capture of a matrix code allowing the performance of the equipment to be monitored and analyzed. The historical performance of the equipment and/or analytical results are made available to the owner/operator of the equipment allowing the owner/operator to re-calibrate the equipment if required.

Although embodiments have been described, those of skill in the art will appreciate that variations and modifications may be made without departing from the scope of the appended claims.

What is claimed is:
1. A method comprising:
obtaining performance data of a communicatively-insulated device;
converting the performance data into a scannable code;
capturing an image of the scannable code;
decoding the scannable code using a communicatively-enabled device to extract an address string encoded in the scannable code, the address string comprising an address of a remote server and the performance data;
initiating, by the communicatively-enabled device, a communications link with the remote server using the address string thereby to provide the performance data to the remote server;
performing, by the remote server, analytics on the performance data; and
sending historic device performance data and/or analytical results to a remote computing device and/or sending a link to the historic device performance data and/or analytical results to the remote computing device;
wherein the communicatively-insulated device is medical imaging equipment and wherein obtaining the performance data comprises scanning a phantom using the medical imaging equipment and/or acquiring medical imaging equipment sensor data and generating a system status report identifying one or more operational parameters of the medical imaging equipment.

2. The method of claim 1, further comprising, prior to the converting, encoding the performance data.

3. The method of claim 2, wherein the encoding comprises serializing the performance data and transforming the serialized performance data to tamper-proof the performance data.

4. The method of claim 3, wherein transforming the serialized performance data comprises subjecting the serialized performance data to one of a check sum function or encryption program.

5. The method of claim 4, wherein the subjecting comprises subjecting the serialized performance data to the check sum function to generate a digital signature that is appended to the serialized performance data.

6. The method of claim 5, wherein the encoding further comprises sanitizing the transformed serialized performance data into an address string format and prepending the address of the remote server to the sanitized performance data thereby to form the address string.

7. The method of claim 1, wherein the scannable code is a matrix code.

8. The method of claim 7, wherein the matrix code is a quick response (QR) code.

9. The method of claim 1, further comprising, after the converting, presenting the scannable code on a display console of the communicatively-insulated device and/or printing the scannable code on a physical medium.

10. The method of claim 1, further comprising capturing the image of the scannable code with the communicatively-enabled device.

* * * * *